United States Patent [19]

Perrault

[11] Patent Number: 4,958,963
[45] Date of Patent: Sep. 25, 1990

[54] MOBILE WORK STATION FOR PODIATRIST

[76] Inventor: Ronald Perrault, 3, avenue des Sapins, Notre-Dame des Prairies, Province de Québec, J6E 1C3, Canada

[21] Appl. No.: 440,748

[22] Filed: Nov. 24, 1989

[51] Int. Cl.⁵ .................................................. A61C 1/02
[52] U.S. Cl. ........................................ 408/56; 408/124; 408/702; 433/77; 433/79; 433/98
[58] Field of Search .................... 408/31, 42, 56, 61, 408/124, 702, 77; 433/77, 79, 98

[56] References Cited

U.S. PATENT DOCUMENTS

| | | | |
|---|---|---|---|
| 3,084,439 | 4/1963 | Staunt | 433/98 |
| 3,210,846 | 10/1965 | Balkin | 433/79 |
| 3,518,763 | 7/1970 | Weiss et al. | 433/79 |
| 3,556,669 | 1/1971 | Valeska et al. | 433/98 |
| 3,718,972 | 3/1973 | Fox et al. | 433/77 |
| 4,332,555 | 6/1982 | Richardson | 433/98 |
| 4,797,098 | 1/1989 | Kawata | 433/98 |

FOREIGN PATENT DOCUMENTS

| | | | |
|---|---|---|---|
| 1566200 | 4/1970 | Fed. Rep. of Germany | 433/98 |
| 1446033 | 8/1976 | United Kingdom | 433/98 |

Primary Examiner—Daniel W. Howell

[57] ABSTRACT

An apparatus for assisting a podiatrist in the performance of various para-medical operations on patients. The apparatus consists of a unit movble on the ground as if a dental unit used by dentists. The work unit includes a pneumatic network, connected to an external air compressor, and to which is connected three tools. Two of these tools include drilling heads, pressurized water outlets and pressurized air outlets, while the third tool includes a pressurized water outlet and pressurized air outlet. Operation of each tool, and of each outlet and drill of a given tool, is made independently of each other, and controlled by a number of knobs, buttons and dials.

1 Claim, 2 Drawing Sheets

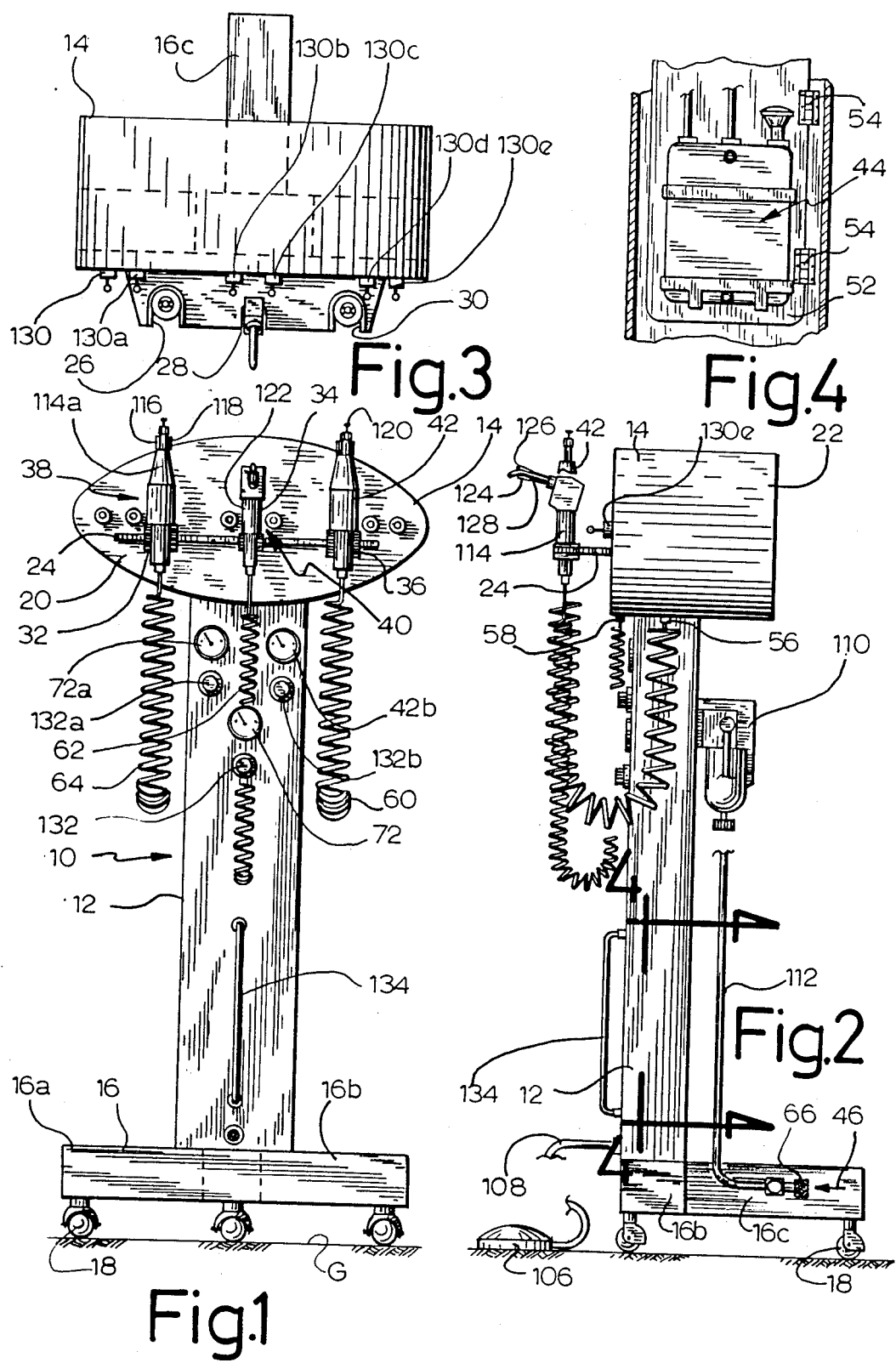

MOBILE WORK STATION FOR PODIATRIST

FIELD OF THE INVENTION

This invention relates to accessories for para-medical practitioners, especially podiatrists.

BACKGROUND OF THE INVENTION

A podiatrist is a para-medical officer who diagnoses and treats disorders of the human foot. Podiatrists therefore require suitable tools to be efficient in their work. In the past, very few such tools were available specifically for podiatrists. Their efficiency may have thus suffered, and their patient may not have been as satisfied as they would have expected.

OBJECTS OF THE INVENTION

The prime goal of the invention is to provide a unitary work station for the podiatrist.

A further object of the invention is the versatility of the work station, which will meet the podiatrist daily routine work needs as well as those needs for minor surgery.

Another object of the invention is that of the high level of safety of operation of the work station.

A further object of the invention is the thoroughness and speed of work it enables the podiatrist to perform.

An object of the invention is to reduce if not eliminate the pain sustained by the patient during operations associated with the work of a podiatrist.

SUMMARY OF THE INVENTION

In view of the stated objects of the invention, there is disclosed a work station for enabling a podiatrist to perform a variety of para-medical operations and adapted to be operatively connected to an external gas compressor, said work station consisting of: a large frame, compressor gas inlet means mounted to said large frame, a closed tank containing a liquid, coupling means for connecting said tank to said air inlet means at least one drilling tool operatively connected to said gas inlet means and defining a drilling head and first and second nozzles, first feed means to feed pressurized gas to said first nozzle, second feed means to feed pressurized water to said second nozzle, and power means to rotate said drilling head, said power means actuated by said gas inlet means.

Preferably, said frame is freely supported in upright position over ground by a base provided with idle casters. Said gaz can be air, and then there could be further included an air filtering device, mounted about said air inlet means. Similarly, said liquid could be water, and then said tank would be characterized in that at least its interior wall be made of stainless steel.

Advantageously, a second tool is provided, being operatively connected to said gas inlet means and defining third and fourth nozzles, third feed means to feed pressurized gas to said third nozzle, and fourth feed means to feed pressurized water to said fourth nozzle. A number of valves and on/off switches would then be envisioned to operate the valves to control said first to fourth feed means and said power means.

First valve means preferably controls the gas pressure about said gas inlet means and second valve means controls the liquid pressure about said liquid tank, said first and second valve means enabling continuous adjustment of the gas and liquid pressures respectively, and pressure gauges monitor said pressures.

It is desirable to add a stay, anchored to the upper section of said frame for supporting said at least one tool which is substantially tubular in upright position; said at least one tool being operatively connected to said frame by a spiral hose made form a flexible material and forming part of said feed means.

Should there be two said drilling tools, each would have two independent gas and liquid feeding means, and there would then be further included a cut-out device which could releasably stop all gas and liquid circulation to all said tools.

BRIEF DESCRIPTION OF THE DRAWINGS

FIGS. 1 and 2 are front and side elevational views respectively of a preferred embodiment of an apparatus for podiatrist in accordance with the invention;

FIG. 3 is a top plan view of the apparatus of FIG. 1;

FIG. 4 is a vertical sectional view taken along line 4—4 of FIG. 2; and

DETAILED DESCRIPTION OF THE INVENTION

Figure 5:
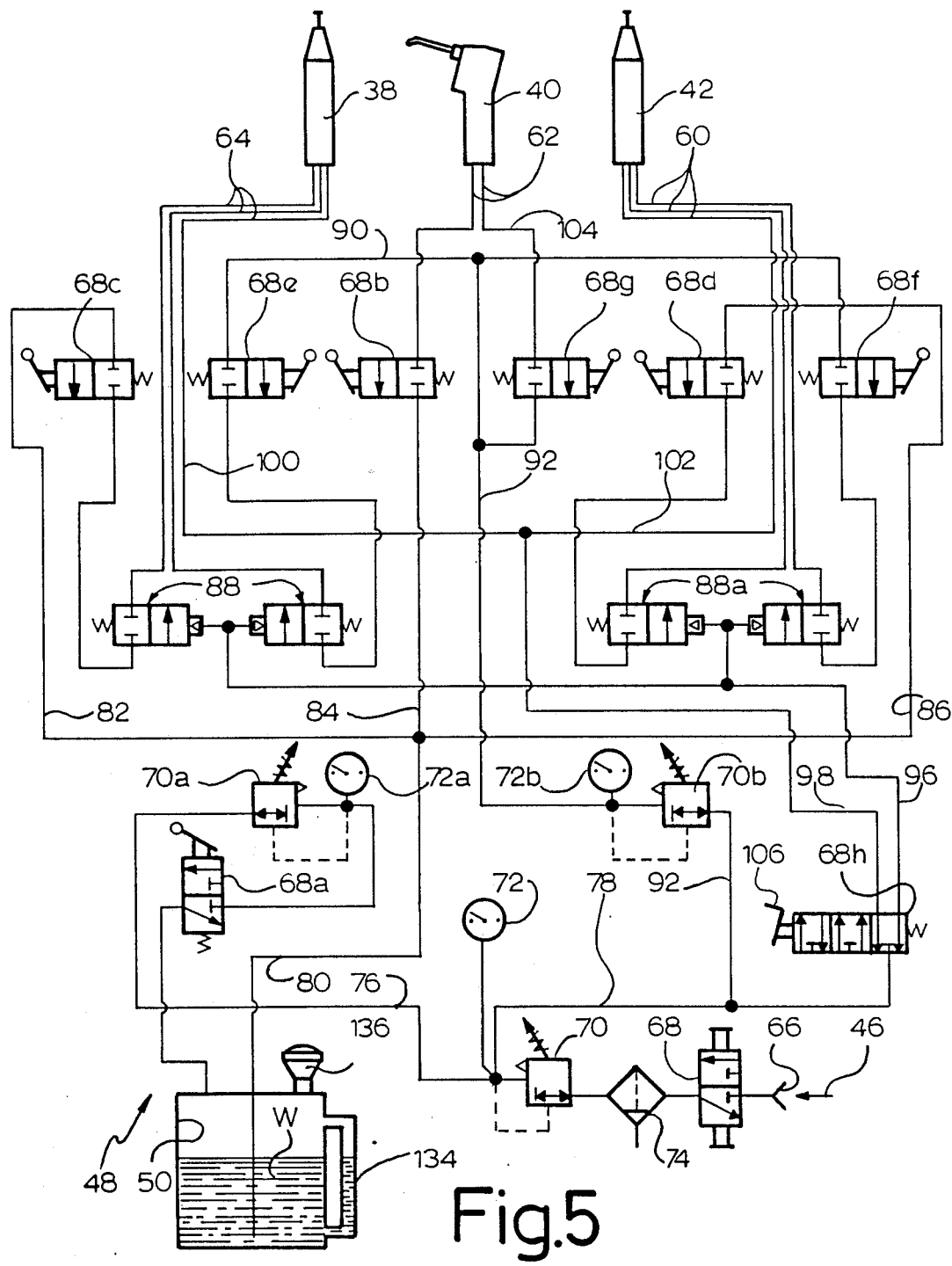
FIG. 5 is a schematic view of the pneumatic network of the apparatus of FIG. 1.

The podiatrist unit 10 includes a wide post member 12 bearing at its top end a large casing 14 and supported over ground G at its bottom end by a T-shaped base 16 provided with three ground-engaging swivel casters 18 at the ends of its three legs 16a, 16b, 16c. Legs 16a, 16b, 16c are square in cross-section, while post 12 is rectangular in cross-section and rests on the inner merging sections of side legs 16a, 16b. Casing 14 is elliptical in transverse cross-section and defines front and rear flat walls 20, 22. Front wall 20 carries a transverse horizontal stay plate 24 at its middle section. Stay 24 defines three transverse arcuate spaced cavities 26, 28, 30 reinforced by vertical collars 32, 34, 36 extending respectively therethrough. Collars 32 and 36 support drilling tools 38 and 42, while the intermediate collar 34 supports a cleansing tool 40, all tools in vertical position.

As such, it is readily apparent that the apparatus or work station 10 looks very much like a dental unit used by doctors in dentistry to assist in the performance of their work.

Each tool 38, 40, 42 is independently operatively connected to both a liquid supply source 44 and to a gazeous supply source 46, via a pneumatic tubing network 48 (see FIG. 5). Liquid source 44 should be sterilized or demineralized water W, stored into a stainless steel tank 50 anchored into the hollow of post 12, while the gaseous source 46 should be pressurized air from an external compressor unit (not shown). Access to water tank 50 is made possible by a flap 52 hinged at 54 to an opening made in the rear wall 12a of post 12, for refilling purposes.

Thus, as we will see, apparatus 10 works solely under pneumatic forces, no electrical outlet being required.

Tools 38, 40, 42 are each connected to casing 14 by inlet ports 56, 58, (56) fixedly mounted on the underside of closed casing 14, by reinforced flexible spiral hoses 60, 62, 64.

A pressurized air pipe (not shown) is engaged in an inlet port 66 anchored into the hollow of base leg 16c. A control valve 68 controls entry of pressurized air inflow, with a safety valve 70 being provided to manually vary the air flow pressure to an acceptable level, as visually measured by a pressure gauge 72. An air filtering device 74 is also provided proximate valve 68. A first air line 76 feeds pressurized air to water tank 50, while a second air line 78 feeds pressurized air to tools 38, 40, 42. From tank 50, a water line 80 feeds pressurized water to tools 38, 40, 42. A second set of control valve 68a, safety valve 70a and air pressure gauge 72a is provided on line 76. Line 80 divides into three lines 82, 84, 86 to feed water to tools 38, 40, 42. A control valve 68b is provided on water line 84. To each water line 82, 86 is provided a similar control valve 68c, 68d respectively, and a cut-out valve system 88, 88a respectively, the latter being able to releasably block circulation of water and air to the drill tools. Two other respective control valves 68e, 68f are provided on the line 90 interconnecting valve systems 88, 88a.

Pressurized air line 78 divides in two lines: line 92 feeding tool 40, and line 94 feeding tools 38 and 42. A control valve 68g is provided on line 94, from which escapes two lines 96 and 98. Line 96 extends towards and operatively interconnect valve systems 88 and 88a. Line 98 divides into two lines 100, 102 to feed tools 38, 42 respectively. To air line 92 is provided a safety valve 70b and an air pressure gauge 72b. Air flow from line 92 is controled by a valve 68h mounted in parallel thereto via line 104, the latter being directly connected to tool 40 while the extension of line 92 merges with line 90.

Hence, the spiral flexible hose 60 of tool 42 carries lines 86, 90 and 102; flexible hose 62 of tool 40, lines 84 and 104; and flexible hose 64 of tool 38, lines 82, 90 and 100; which is to say, line 90 is common to both tools 38 and 42. Tools 38 and 42 are similar to each other, and each includes a main tubular body 114 having an upper conical section 114a, a pressurized air nozzle 116 and a pressurized water nozzle 118 above the conical section 114a, and a topmost drill 120; nozzles 116-118 of tools 38 and 42 are connected to lines 82, 100 and 86, 102 respectively, while drill 120 is operatively connected (i.e. its conventional turbine is rotatively powered) by the pressurized air from lines 100, 102. The turbine of drills 120 of tools 38, 42 should be able to rotate up to 40,000 times a minute (rpm) under the impulse of the pressurized air. Tool 40 has also a tubular body 122, but with an extended spout 124 transverse to body 122 and defining a pressurized air nozzle 126 and a pressurized water nozzle 128 integrally mounted into spout 124; nozzle 126 being fed by line 84.

Preferably, control valve 68g is embodied in a ground standing foot pedal 106, connected to post 12 by flexible hose 108; while control valve 68a is embodied in a housing 110 anchored to post 12 and connected to socket 66 by flexible hose 112.

Dials 72, 72a, 72b are mounted on the front wall of post 12, for convenience of the operator. Advantageously, valves 68c, 68e, 68b, 68g, 68d, 68f are controlled in discrete fashion by pivotable knobs 130, 130a, 130b, 130c, 130d, 130e mounted on the front wall 20 of the upper casing 14, for on/off actuation of the valves. Safety valves 70, 70a, 70b are in turn controlled in continuous fashion by rotatable buttons 132, 132a, 132b mounted to post 12 proximate their corresponding dials 72, 72a, 72b respectively.

Profitably, water tank 50 has a lateral liquid level transparent elbow 134, to indicate the remaining water level therein, and a top pressure outlet duct 136, to allow escape of air pressure beyond a given safety level, e.g. in the case where internal tank pressure is substantially increased due to high ambient temperature or to abnormaly high air pressure coming from the external air compressor 46, to prevent the tank walls from bursting.

It can now be understood that the nozzles of each tool 38, 40, 42 can eject water, air, or a combination of water and air under pressure, and each tool 38, 42 can drive the turbine of its corresponding drill head, at variable rates independently of each other, depending upon the adjustment made with front buttons 132-132a-132b. Cleansing tool 40 is used to clean the legs and feet of the patient with water and or air and to asepticize same before use of the drilling tools 38 and 42. The drills of the drilling tools 38, 42 have two functions:

(a) to slit up a nail up to its membrane or bed without damaging the vascular tissues, with the end drills being rotated at variable adjustable speeds (up to 40,000 rpm) and driven by rotatable turbines within the tools 38, 42;

(b) for the incision of hyperkeratosis, of keratosis, or nucleated or non nucleated keratosis, of soft bodies and also for minor surgeries by minimal incision and by scraping cartilage or bones.

The pressurized water generated by the nozzles on the drilling tools not only reduces the temperature at the surface of the nail, which temperature will raise due to the friction of the rotating drill thereon, but also prevents the nail powder or dust produced by the incision of the nail to raise in the air, by projecting the dust on the ground and combining with it to form a sludge which will remain on the ground. The pressurized air also assists in the removal of the nail powder.

It is important to prevent the nail powder from floating in the air, since it may very well contain microscopic mushrooms such as those resulting from medical conditions such as mycosis, onychogriphose, onychomycose, etc... (which is why the patient consults a podiatrist) wherein these mushrooms are toxic to the patient or his podiatrist if inhaled thereby constituting a health hazard.

The present apparatus for podiatrist is characterized by the thoroughness and speed of work it enables the podiatrist to perform, by its versatile qualities from podiatrist routine to surgical operations, by its safety of operation for the podiatrist and his patient since no electric current is involved in the operation of the work station and also no dust of nail powder can be inhaled by the persons in the room of the apparatus 10, and by the fact that no pain whatsoever can be felt by the patient when the apparatus is used due to its principle of construction.

I claim:

1. A work station for podiatrist comprising:
   (a) a large, rigid frame;
   (b) compressed air feed means, having an outlet integral to said frame;
   (c) a water-containing tank, integral to said frame;
   (d) at least a first and second turbine drill members, to be connected to the compressed air feed means outlet and water tank, and movable away from the frame;
   (e) at least one spray gun, to be connected also to the compressed air feed means and water tank, movable away from the frame;
   (f) a pneumatic tubing network, operatively connecting said drill members and spray gun to said compressed air feed means outlet and water tank, said network defining a main line means, feeding water from said water tank to each drill member and spray gun through a corresponding one of a first series of water lines, and also feeding pressurized air from said compressed air feed means outlet to each drill member and spray gun through a corresponding one of a second series of air lines; wherein operation of each drill member and spray gun is controlled by the flow of water and/or air therethrough;
(g) a number of pneumatically operating, manually controlled, non electromagnetic valve members, including at least one for each said water line and at least one for each said air line;
(h) a foot-pedal actuated, pneumatically operating, non-electromagnetic valve member, operatively connected through connecting means to each said drill member, for controlling operation thereof; wherein said work station works solely by pneumatic forces, with positively no electrical current of any kind being present therewithin, whereby there is no danger whatsoever of electrocution through use of water therein; and wherein the flow of air and water through each said drill members and spray gun is monitored independently of each other by said valve members, at continuous, variable rates.

* * * * *